(12) United States Patent
Stetson

(10) Patent No.: US 7,016,715 B2
(45) Date of Patent: Mar. 21, 2006

(54) SELECTION OF PRESET FILTER PARAMETERS BASED ON SIGNAL QUALITY

(75) Inventor: Paul F. Stetson, Oakland, CA (US)

(73) Assignee: NellcorPuritan Bennett Incorporated, Pleasanton, CA (US)

(*) Notice: Subject to any disclaimer, the term of this patent is extended or adjusted under 35 U.S.C. 154(b) by 0 days.

(21) Appl. No.: 10/341,722

(22) Filed: Jan. 13, 2003

(65) Prior Publication Data
US 2004/0138538 A1 Jul. 15, 2004

(51) Int. Cl.
A61B 5/00 (2006.01)

(52) U.S. Cl. ........................ 600/336; 600/323; 702/191

(58) Field of Classification Search ........ 600/322–323, 600/336; 702/190–191; 375/350; 382/761
See application file for complete search history.

(56) References Cited

U.S. PATENT DOCUMENTS

| 5,506,798 | A | | 4/1996 | Shimada et al. |
| 5,632,272 | A | * | 5/1997 | Diab et al. ................. 600/323 |
| 5,769,785 | A | | 6/1998 | Diab et al. |
| 6,135,952 | A | | 10/2000 | Coetzee |
| 6,142,942 | A | * | 11/2000 | Clark ......................... 600/443 |
| 2002/0003832 | A1 | | 1/2002 | Siefert |
| 2002/0045806 | A1 | | 4/2002 | Baker, Jr. et al. |
| 2002/0099282 | A1 | | 7/2002 | Knobbe et al. |
| 2003/0053617 | A1 | * | 3/2003 | Diethorn ................ 379/406.01 |
| 2003/0223489 | A1 | * | 12/2003 | Smee et al. .................. 375/233 |

* cited by examiner

Primary Examiner—Eric F. Winakur
Assistant Examiner—Matthew Kremer
(74) Attorney, Agent, or Firm—Fletcher Yoder

(57) ABSTRACT

Methods and devices for reducing noise effects in a system for measuring a physiological parameter, including receiving an input signal; obtaining an assessment of the signal quality of the input signal; selecting coefficients for a digital filter using the assessment of signal quality; and filtering the input signal using the digital filter, without comparing the filter's output signal with the input signal.

20 Claims, 2 Drawing Sheets

SELECTION OF PRESET FILTER PARAMETERS BASED ON SIGNAL QUALITY

BACKGROUND OF THE INVENTION

The present invention relates to the processing of signals obtained from a medical diagnostic apparatus, such as a pulse oximeter, using a digital filter to reduce noise effects.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. Most pulse oximeters extract the plethysmographic signal having first determined saturation or pulse rate, both of which are susceptible to interference.

A challenge in pulse oximetry is in analyzing the data to obtain a reliable measure of a physiologic parameter in the presence of large interference sources. Various solutions to this challenge have included methods that assess the quality of the measured parameter and decide on displaying the measured value when it is deemed reliable based upon a signal quality. Another approach involves a heuristic-based signal extraction technology, where the obtained signals are processed based on a series of guesses of the ratio, and which require the algorithm to start with a guess of the ratio, which is an unknown. Both the signal-quality determining and the heuristic signal extraction technologies are attempts at separating out a reliable signal from an unreliable one, one method being a phenomenological one and the other being a heuristic one.

A known approach for the reduction of noise in medical diagnostic devices including pulse oximeters involves the use of an adaptive filter, such as an adaptive digital filter. The adaptive filter is actually a data processing algorithm, and in most typical applications, the filter is a computer program that is executed by a central processor. As such, the filter inherently incorporates discrete-time measurement samples rather than continuous time inputs. A type of digital filter that is used in pulse oximeter systems is a Kalman filter. While conventional adaptive digital filters in general and Kalman filters in particular have been assimilated in medical diagnostics system to help reduce noise in a signal, there are still many challenges that need to be addressed to improve the techniques that are used to reduce noise effects in signals; noise effects such as those present in a medical diagnostic device. One of the shortcomings of using a Kalman filter is that a Kalman filter is an adaptive filter whose functioning is mathematically-based and where its aim is to compare the output of the filter with a desired output, and reduce the error in the comparison by continuously varying the filter's coefficients. So, a Kalman filter generates filter coefficients in an adaptive manner to minimize an error. While this method has been adopted by many, it is still a method that is somewhat blind regarding the signal that it is being filtered. Such an approach does not take into account the unique attributes that an input signal may possess and which are physiologically based. Another shortcoming of the Kalman filtering is that the Kalman filter is linear in its input-output relationship. One can appreciate that in certain conditions, the requirement that the filter be linear in its input-output relationship is too constraining. Yet another shortcoming of a Kalman filter is that filter parameters are continuously tuned, which can be computationally expensive.

There is therefore a need to develop a filter for reducing noise effects in signals that does not suffer form the above-mentioned constraints of conventional adaptive filters.

BRIEF SUMMARY OF THE INVENTION

The present invention is directed towards methods and devices for reducing noise effects in a system for measuring a physiological parameter, including receiving an input signal; obtaining an assessment of the signal quality of the input signal; selecting coefficients for a digital filter using the assessment of signal quality; and filtering the input signal using the digital filter, without comparing the filter's output signal with the input signal.

In certain aspects, the filter coefficients are selected from a plurality of discrete preset values. In certain embodiments, the discrete and preset values are fixed or non-changing values. The digital filter can have either a linear or preferably a non-linear input-output relationship.

In pulse oximetry applications, the quality of the input signal may be assessed by obtaining or measuring signal parameters that include the skew of the time derivative of the signal; the correlation between signals from different wavelengths; the variation in signal amplitude, as well as others. Other assessments, such as maximum values or spectral peak frequencies, may also be used in determining filter parameters.

In some embodiments, the selection of filter parameters or coefficients is performed in real time, with the coefficients of the digital filter being determined using a current input sample. In certain other embodiments, the selection of filter parameters is performed using a previously stored input signal sample.

In pulse oximetry applications, the input signals can be a function of an oxygen saturation, or a pulse rate. Furthermore, these signals correspond with sensed optical energies from a plurality of wavelengths.

For a further understanding of the nature and advantages of the invention, reference should be made to the following description taken in conjunction with the accompanying drawings.

DETAILED DESCRIPTION OF THE INVENTION

The methods and systems in accordance with embodiments of the present invention are directed towards selecting and adjusting the parameters of a digital filter based an assessment of the quality of the input signals to the filter. The invention is particularly applicable to and will be explained by reference to measurements of oxygen saturation of hemoglobin in arterial blood and patient heart rate, as in pulse oximeter monitors and pulse oximetry sensors. However, it should be realized the invention is equally applicable to any generalized patient monitor and associated patient sensor, such as ECG, blood pressure, temperature, etc., and is not to be limited for use only with oximetry or pulse oximetry.

Figure 1:
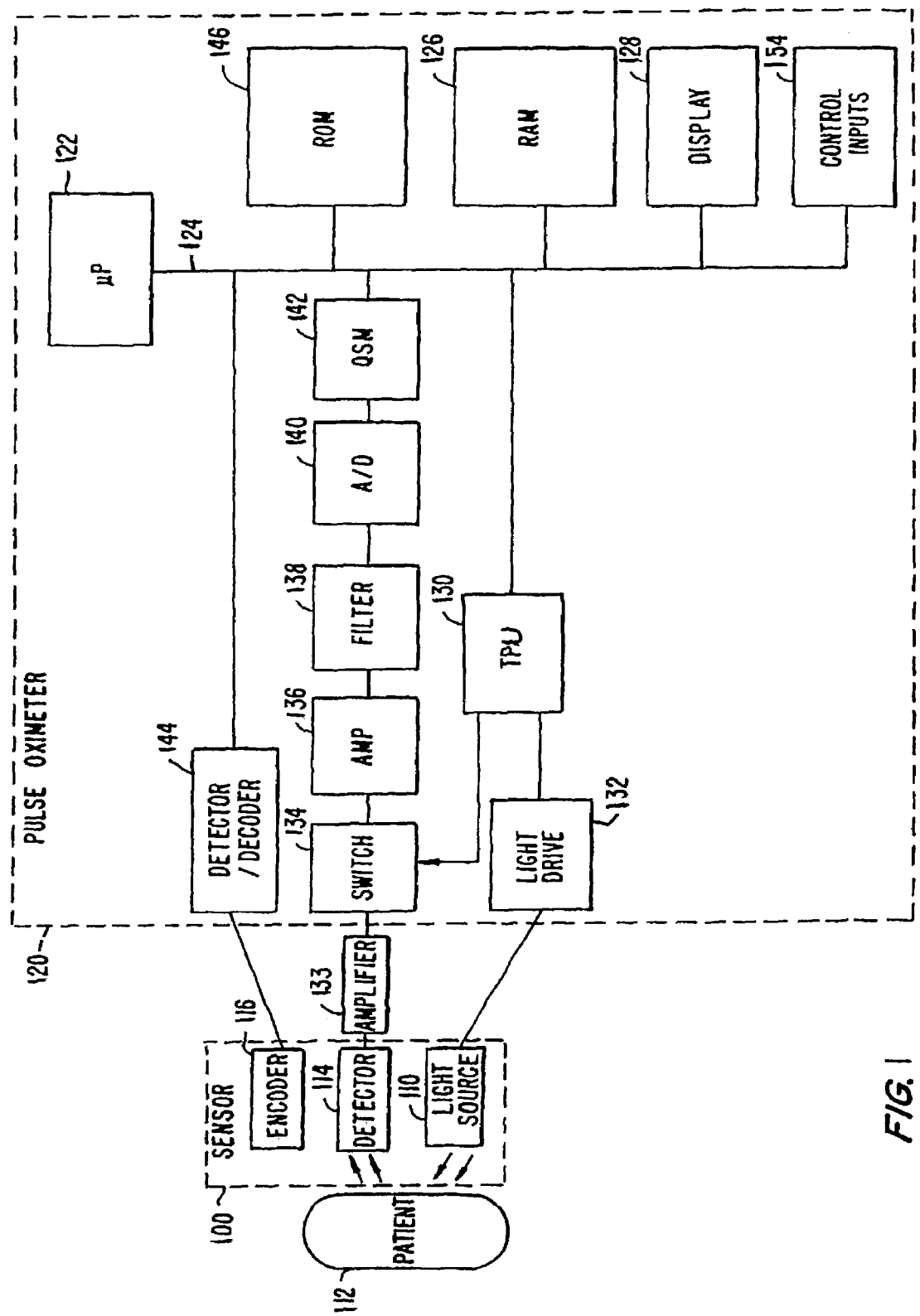
FIG. 1 is a block diagram of an exemplary oximeter.

FIG. 1 is a block diagram of one embodiment of a pulse oximeter that may be configured to implement the embodiments of present invention. The filter embodiments of the present invention can be a data processing algorithm that is executed by the microprocessor 122, described below. Light from light source 110 passes into patient tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier filter and AID converters for multiple light wavelengths or spectrums received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectrums is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The brief description of an exemplary pulse oximeter set forth above, serves as a contextual fabric for describing the methods for reducing noise effects in the received signals according to embodiments of the present invention, which are described below. The embodiments of the present invention, which are used to reduce the noise effects in the signal using an assessment of the quality of the input signal, are described below in conjunction with the block diagram of FIG. 2.

A signal quality indicator is a measured parameter that is capable of estimating the reliability and accuracy of a signal. For example, when measuring blood oxygen saturation using a pulse oximeter, a signal quality indicator is able to indirectly assess whether an estimate of a value of blood oxygen saturation is an accurate one. This determination of accuracy is made possible by a thorough and detailed study of volumes of measured values and various indicators to determine which indicators are indicative of signal quality and what, if any, is the correlation between the indicator and the accuracy of the estimated value.

In pulse oximetry, examples of signal quality indicators include the skew of the time derivative of the signal; the correlation between signals from different wavelengths; the variation in signal amplitude, as well as others. Other assessments, such as maximum values or spectral peak frequencies, may also be used in determining filter parameters. In addition to these signal quality indicators, other signal quality indicators may also be used for the selection of filter coefficients. In pulse oximetry, these additional signal quality indicators include: a signal measure indicative of the degree of similarity of an infrared and red waveforms; a signal measure indicative of a low light level; a signal measure indicative of an arterial pulse shape; a signal measure indicative of the high frequency signal component in the measure value; a signal measure indicative of a consistency of a pulse shape; a signal measure indicative of an arterial pulse amplitude; a signal measure indicative of modulation ratios of red to infrared modulations and a signal measure indicative of a period of an arterial pulse. These various indicators provide for an indirect assessments of the presence of known error sources in pulse oximetry measurements, which include optical interference between the sensor and the tissue location; light modulation by other than the patient's pulsatile tissue bed; physical movement of the patient and improper tissue-to-sensor positioning. These additional signal quality indicators are described in further detail in a co-pending U.S. patent application entitled: "SIGNAL QUALITY METRICS DESIGN FOR QUALIFYING DATA FOR A PHYSIOLOGICAL MONITOR," U.S. Ser. No. 10/341,318, filed Jan. 10, 2003, the patent application of which is herein incorporated by reference in its entirety for all purposes.

Figure 2:
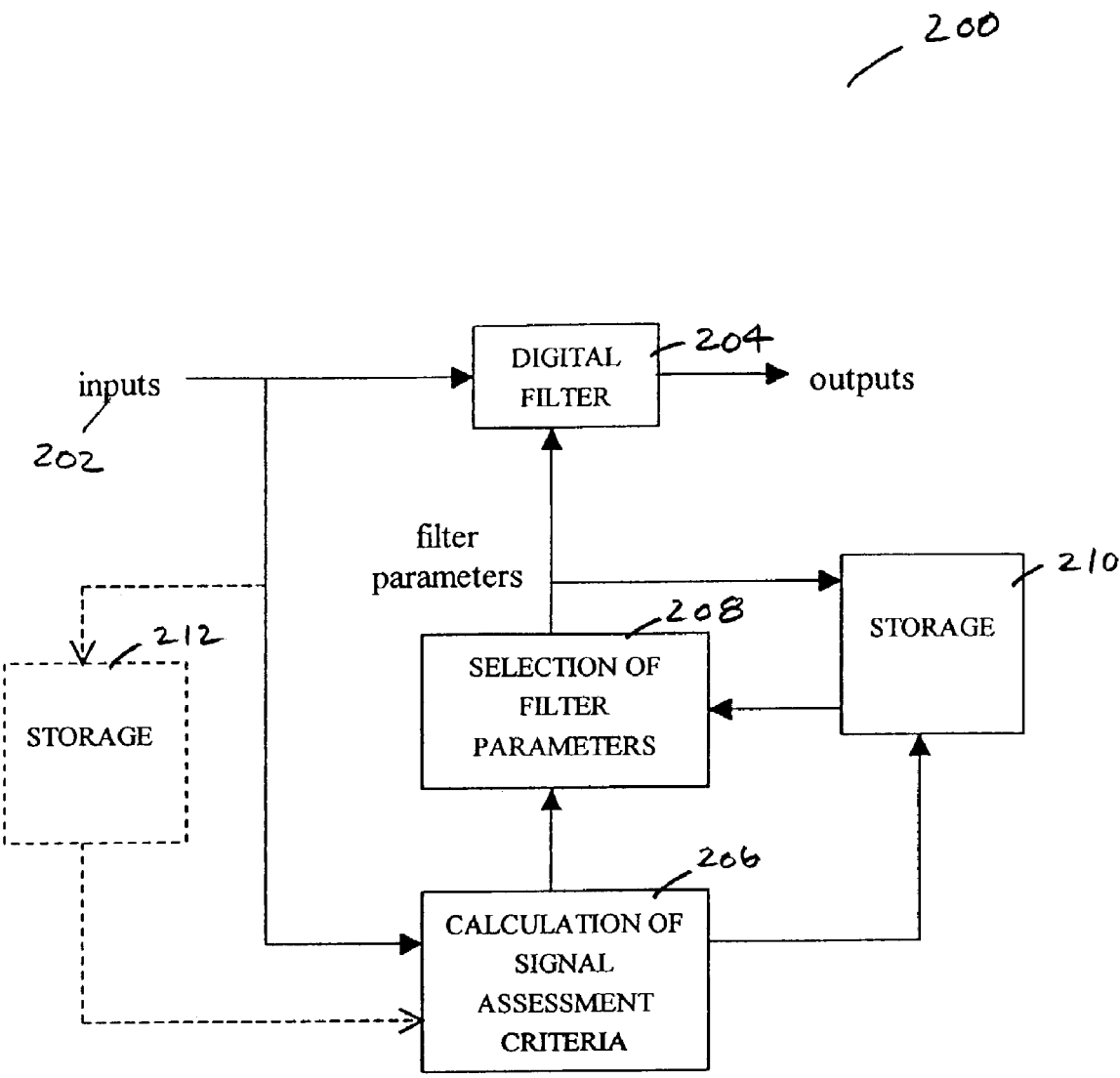
FIG. 2 is a block diagram depicting the operation of the signal-quality-based filter operation in accordance with embodiments of the present invention.

FIG. 2 is a block diagram 200 depicting the operation of the signal-quality-based selection of filter parameters in accordance with embodiments of the present invention. In one embodiment, the digital filter is a linear filter. For a linear filter is chosen, the filter can have either a finite or an infinite impulse response. Alternately, the filter may be a non-linear filter. Inputs 202 are applied to the digital filter 204 and to a signal quality assessment subsystem 206 that assesses how noisy the inputs look. Subsystem 206 calculates various signal quality metrics and provides the information to the selection subsystem 208, which selects filter parameters according to the criteria calculated by the signal quality subsystem 206. Storage subsystem 210 interfaces with the subsystems 206 and 208 to store and provide signal quality metrics as well as filter parameters. In one embodiment, the selection of filter parameters is performed in real time, with the filter parameters being determined using current input samples.

In an alternate embodiment, the filter parameters are calculated using a buffer 212 of recent input samples. In addition, signal assessment criteria and filter parameters can also be held in storage 210 for reference or for use in the calculation of new values.

As set forth above, various signal quality indicators may be used to select filter parameters. Additionally, the selection of the filter parameters may be based on more than one signal quality indicator. Furthermore, the selection of the filter parameters may be based on the output of an algorithm that combines several signal quality indicators. In one embodiment in an oximeter system, the variance in the raw saturation value is used to determine the filter's smoothing coefficients. In this embodiment, the selection is achieved by comparing the variance in the raw sat signal to several thresholds, and the filter's smoothing coefficients are selected depending on which range the variance falls in.

In an alternate embodiment in an oximeter system used for average pulse estimation, the filter parameter selection algorithm uses a combination of various signal quality metrics, Z to select values for filter coefficients for the digital filter, where $$Z = w_1 * SQ1 + w_2 * SQ2 + w_3 * SQ3, \text{ where}$$

$w_1$, $w_2$, and $w_3$ are weighting factors

SQ1 is a measure of the variance in the raw saturation signal

SQ2 is a measure of the correlation between signals from different wavelengths

SQ3 is a measure of the skew of the derivative waveform

Yet alternately, instead of using Z to select the filter coefficients, a non-linear function of Z can be used to select a coefficient or coefficients for the filter. In operation, the selection algorithm may first be tuned before it is fully implemented in a particular diagnostics system. The tuning of the selection algorithm(s) may be done manually using heuristic approaches. Alternately, the selection algorithm may be tuned statistically, in a manner similar to training a neural network.

Embodiments of the present invention offer several advantages over conventional adaptive filtering. It is known that conventional adaptive filtering seeks to optimize some output criterion by continuously tuning the coefficients in a linear filter. The approach as embodied by the present invention is advantageous over conventional adaptive filtering for the following reasons. First, filter parameters in accordance with embodiments of the present invention are selected by switching among several preset or fixed values, rather than being varied or tuned continuously. By switching the parameters of the digital filter among fixed, preset values, the embodiments of the present invention provide for computational savings and simplicity of implementation. Second, the parameters of the digital filter are selected based upon an assessment of the input signal received by the filter rather than by comparing the filter's output with its input. This too, provides for computational savings and simplicity of implementation. Third, the filter need not be a linear filter, that is the filter is not required to be linear in its input-output relationship. Since the filter in accordance with embodiments of the present invention is not constrained to be linear, the filter's design can correspond more to physiological than to mathematical requirements, as is the case with most conventional adaptive filtering schemes. This physiological-based filter parameter selection may be used to, for example, attenuate pulse amplitudes above a threshold, or respond more quickly to decreases than to increases in blood oxygen saturation.

Accordingly, as will be understood by those of skill in the art, the present invention which is related to reducing noise effects in a system for measuring a physiological parameter, may be embodied in other specific forms without departing from the essential characteristics thereof. For example, signals indicative of any physiological parameter other than oxygen saturation, such as pulse rate, blood pressure, temperature, or any other physiological variable could be filtered using the techniques of the present invention. Moreover, many other indicators of the quality of the input signal can be used as a basis for the selection of the filter's coefficients. Further, while the present embodiments have been described in the time-domain, frequency-based methods are equally relevant to the embodiments of the present invention. Accordingly, the foregoing disclosure is intended to be illustrative, but not limiting, of the scope of the invention, which is set forth in the following claims.

What is claimed is:

1. In a system for measuring a physiological parameter, a method of reducing noise effects, comprising:
   receiving input signals of more than one wavelength;
   obtaining an assessment of the signal quality of the input signals by obtaining a measure of the correlation between the signals of different wavelengths;
   selecting coefficients for a digital filter using the assessment of signal quality; and
   filtering the input signals using the digital filter, without comparing the filter's output signal with the input signals.

2. The method of claim 1 wherein selecting comprises selecting coefficients from a plurality of discrete preset values.

3. The method of claim 1 wherein selecting comprises selecting coefficients from a plurality of constant and preset values.

4. The method of claim 1 wherein filtering comprises operating a digital filter having a linear input-output relationship.

5. The method of claim 1 wherein filtering comprises operating a digital filter having a non-linear input-output relationship.

6. The method of claim 1 wherein selecting is performed in real time, with the coefficients of the digital filter being determined using a current input sample.

7. The method of claim 1 wherein selecting is performed using a previously stored input signal sample.

8. The method of claim 1 wherein receiving comprises receiving signals from an oximeter, wherein the signals are a function of an oxygen saturation.

9. The method of claim 1 wherein receiving comprises receiving signals from an oximeter, wherein the signals are a function of a pulse rate.

10. The method of claim 1 wherein receiving the input signals comprises receiving signals corresponding to sensed optical energies from a plurality of wavelengths.

11. In a system for a measuring a physiological parameter, an apparatus for reducing noise effects, comprising:
    means for receiving input signals of more than one wavelength;

means for obtaining an assessment of the signal quality of the input signals by obtaining a measure of the correlation between the signals of different wavelengths;

means for selecting coefficients for a digital filter using the assessment of signal quality; and means for filtering the input signals using the digital filter, without comparing the filter's output signal with said input signals.

12. The apparatus of claim 11 wherein the means for selecting are configured to select the coefficients from a plurality of discrete preset values.

13. The apparatus of claim 11 wherein the means for selecting are configured to select the coefficients from a plurality of constant and preset values.

14. The apparatus of claim 11 wherein the means for filtering comprise a digital filter having a linear input-output relationship.

15. The apparatus of claim 11 wherein the means for filtering comprise a digital filter having a non-linear input-output relationship.

16. The apparatus of claim 11 wherein the means for selecting are configured to select the coefficients in real time, with the coefficients for the digital filter being determined using a current input sample.

17. The apparatus of claim 11 wherein the means for selecting are configured to select the coefficients using a previously stored input signal sample.

18. The apparatus of claim 11 wherein the means for receiving are configured to receive signals from an oximeter, wherein the signals are a function of an oxygen saturation.

19. The apparatus of claim 11 wherein the means for receiving are configured to receive signals from an oximeter, wherein the signals are a function of a pulse rate.

20. The apparatus of claim 11 wherein the means for receiving are configured to receive signals corresponding to sensed optical energies from a plurality of wavelengths.

* * * * *